United States Patent
Khouri

(12) 
(10) Patent No.: US 6,500,112 B1
(45) Date of Patent: *Dec. 31, 2002

(54) VACUUM DOME WITH SUPPORTING RIM AND RIM CUSHION

(75) Inventor: Roger K. Khouri, St. Louis, MO (US)

(73) Assignee: Brava, LLC, Coconut Grove, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/141,460

(22) Filed: Aug. 27, 1998

Related U.S. Application Data

(63) Continuation of application No. 08/698,941, filed on Aug. 16, 1996, now abandoned, which is a continuation-in-part of application No. 08/516,623, filed on Aug. 18, 1995, now Pat. No. 5,676,634, which is a continuation-in-part of application No. 08/504,640, filed on Jul. 20, 1995, now Pat. No. 5,695,445, which is a continuation of application No. 08/220,186, filed on Mar. 30, 1994, now Pat. No. 5,536,233.

(51) Int. Cl.$^7$ .................................................. A61F 5/00
(52) U.S. Cl. ........................................... 600/38; 601/14
(58) Field of Search .................. 600/38–41; 601/6–14; 623/7, 15; 606/213, 245

(56) References Cited

U.S. PATENT DOCUMENTS

| | | |
|---|---|---|
| 532,236 A | 1/1895 | Hardesty |
| 936,434 A | 10/1909 | Eganhouse |
| 1,021,688 A | 3/1912 | Jeune |
| 1,312,619 A | 8/1919 | D'Orsay |
| 1,472,234 A | 10/1923 | Thomas |
| 2,012,755 A | 8/1935 | De Muth |
| 2,616,417 A | 11/1952 | Holbrook |
| 2,817,333 A | 12/1957 | Cole |
| 3,174,851 A | 3/1965 | Buehler et al. |
| 3,382,867 A | 5/1968 | Reaves |
| 3,568,675 A | * 3/1971 | Harvey |

(List continued on next page.)

FOREIGN PATENT DOCUMENTS

| | | |
|---|---|---|
| EP | WO91/17727 | 11/1991 |
| WO | WO 93/0927 | 5/1993 |

OTHER PUBLICATIONS

Copy of *Enlargement Book*, ©1990 Topco Books.

Copy of *An Anthology of Plastic Surgery*, edited by Harry Hayes, Jr., M.D., specifically Section 6 entitled "Quackery and Nostrums", Aspen Publishers, Inc., 1986, pp. 163–175.

Article entitled "The Tension–Stress Effect on the Genesis and Growth of Tissues—Part I. The Influence of Stability of Fixation and Soft–Tissue Preservation" by Gavriil A. Ilizarov, AM., M.D., Ph.D., from *Clinical Orthopaedics and Related Research*, from Section III, entitled "Basic Science And Pathology", No. 238, Jan. 1989, pp. 249–281.

(List continued on next page.)

*Primary Examiner*—John P. Lacyk
(74) *Attorney, Agent, or Firm*—Howell & Haferkamp, L.C.

(57) ABSTRACT

A dome for applying a vacuum to a patient's skin surface is comprised of a generally rigid dome capable of withstanding a pressure differential, with a rim cushion underlying the rim of the dome for supporting a rim from the patient's skin surface. The rim may be generally wider than the dome in order to distribute the attendant forces across a greater surface and avoid tissue damage. A sticky sole underlies the rim cushion and seals the rim cushion to the patient's skin to thereby preserve the vacuum within the dome. The sticky sole may be comprised of any adhesive material or even be achieved through the use of an appropriate material for the rim cushion itself.

14 Claims, 6 Drawing Sheets

U.S. PATENT DOCUMENTS

| | | |
|---|---|---|
| 3,631,853 A | 1/1972 | Burdette, Jr. |
| 3,785,369 A | 1/1974 | Tallent |
| 3,859,989 A | 1/1975 | Spielberg |
| 3,874,387 A | 4/1975 | Barbieri |
| 3,908,662 A | 9/1975 | Razgulov et al. |
| 3,939,827 A | 2/1976 | Brunstetter |
| 4,175,554 A | 11/1979 | Gerow |
| 4,368,883 A | 1/1983 | Titkin |
| 4,633,865 A | 1/1987 | Hengstberger et al. |
| 4,653,484 A | 3/1987 | Cannon |
| 4,706,661 A | 11/1987 | Barrett |
| 4,718,411 A | 1/1988 | Stewart |
| 4,770,176 A | 9/1988 | McGreevy et al. |
| 4,774,091 A | 9/1988 | Yamahira et al. |
| 4,834,110 A | 5/1989 | Richard |
| 4,856,498 A | 8/1989 | Osbon |
| 4,856,499 A | 8/1989 | Kelly |
| 4,930,674 A | 6/1990 | Barak |
| 4,995,381 A | 2/1991 | Marmar et al. |
| 5,059,211 A | 10/1991 | Stack et al. |
| 5,141,516 A | 8/1992 | Detweiler |
| 5,197,978 A | 3/1993 | Hess |
| 5,234,401 A | 8/1993 | Yamanaka |
| 5,254,113 A | 10/1993 | Wilk |
| 5,273,900 A | 12/1993 | Boyce |
| 5,274,074 A | 12/1993 | Tang et al. |
| 5,276,015 A | 1/1994 | Khouri et al. |
| 5,292,802 A | 3/1994 | Rhee et al. |
| 5,308,889 A | 5/1994 | Rhee et al. |
| 5,312,333 A | 5/1994 | Churinetz et al. |
| 5,314,472 A | 5/1994 | Fontaine |
| 5,336,158 A | 8/1994 | Huggins et al. |
| 5,344,396 A | 9/1994 | Clark, Jr. |
| 5,370,685 A | 12/1994 | Stevens |
| 5,464,450 A | 11/1995 | Buscemi et al. |
| 5,468,220 A | 11/1995 | Sucher |
| 5,476,091 A | 12/1995 | Johnson |
| 5,476,478 A | 12/1995 | Jackson |
| 5,533,499 A | 7/1996 | Johnson |
| 5,536,233 A * | 7/1996 | Khouri ..................... 601/14 |
| 5,636,643 A | 6/1997 | Argenta et al. |
| 5,645,081 A | 7/1997 | Argenta et al. |
| 5,653,744 A | 8/1997 | Khouri |
| 5,662,583 A * | 9/1997 | Khouri ..................... 601/14 |
| 5,676,634 A | 10/1997 | Khouri |
| 5,695,445 A | 12/1997 | Khouri |
| 5,701,917 A | 12/1997 | Khouri |
| 5,723,115 A | 3/1998 | Serrero |
| 6,083,912 A | 7/2000 | Khouri |
| 6,086,866 A | 7/2000 | Khouri |

OTHER PUBLICATIONS

Article entitled "The 'Niplette': an instrument for the non–surgical correction of inverted nipples" by D.D. McGeorge, from *British Journal Of Plastic Surgery* 1994, pp. 46–49.

Copy of *How To Enlarge Your Penis*, ©1988 House One, expurgated version.

Brochure entitled "Nipple Enlargement System" by Joel Kaplan, Ph.D., 1993.

Article entitled "The Ilizarov Technique: A Method To Regenerate Bone and Soft Tissue" by Dror Paley, M.D., et al., pp. 1–41.

Article entitled "The Callotasis Method of Limb Lengthening" by Roberto Aldegheri, M.D., et al., from *Clinical Orthopaedics and Related Research*, No. 241, Apr. 1989, pp. 137–145.

Article entitled "Histophathology of Human Expanded Tissue" by Krystyna A. Pasyk, M.D. et al., from *Clinics in Plastic Surgery*, vol. 14, No. 3, Jul. 1987, pp. 435–445.

Article entitled "The Expansion of an Area of Skin by Progressive Distention of a Subcutaneous Balloon—Use of the Method for Securing Skin for Subtotal Reconstruction of the Ear", by Charles G. Neumann, M.D. from *Plastic And Reconstructive Surgery*, Feb. 1957, pp. 124–130.

Article entitled "Tissue Expansion in Soft–Tissue Reconstruction" by Chedomir Radovan, M.D., from *Plastic and Reconstructive Surgery*, Oct. 1984, pp. 482–492.

Article entitled "Elongation of Peripheral Nerve and Viscera Containing Smooth Muscle" by Ernest K. Manders, M.D., et al., from *Clinics in Plastic Surgery*, vol. 14, No. 3, Jul. 1987, pp. 551–562.

Article entitled "Rapid Elongation of Arteries and Veins in Rats with a Tissue Expander" by G. Björn Stark, M.D., et al., from *Plastic And Reconstructive Surgery*, Oct. 1987, pp. 570–581.

Alway, S.E., Winchester, P.K., Davis, M.E., and Gonyea, W. Regionalized adaptations and muscle fiber proliferation in stretch–induced enlargement. Journal of Applied Physiology 66:771, 1989.

Argenta, L.C. Controlled tissue expansion in reconstructive surgery. British Journal of Plastic Surgery 37:520, 1984.

Askill et al., Sutureless Vasovasostomy: New Technique Using Experimental Microclip in Rat Model Urology, vol. 40, No. 2, 191–4, 1992.

Austad, E.D., Thomas, S.B., and Pasyk, K. Tissue Expansion: Dividend or Loan? Plastic and Reconstructive Surgery 78:63, 1986.

Becker, H. Breast Reconstruction Using an Inflatable Breast Implant with Detachable Resevoir. Plastic and. Reconstructive Surgery 73:678, 1984.

Bennett, R.G. and Hirt, M. A History of Tissue Expansion: Concepts, Controversies, and Complications. J. Dermatol Surg. Oncol. 19:1066, 1993.

Bianchi, A. Intestinal Loop Lengthening A Technique for Increasing Small Intestinal Length. Journal of Pediatric Surgery 15:145, 1980.

Björn Stark, M.D., et al., "Rapid Elongation of Arteries and Veins in Rats with a Tissue Expander" from *Plastic And Reconstructive Surgery*, Oct. 1987, pp. 570–581.

Block, M.S., Cervini, D., Chang, A. and Gottsegen, G.B. Anterior Maxillary Advancement Using Tooth–Supported Distraction Osteogenesis. J. Oral Maxillofac. Surg. 53:561, 1995.

Bolinder et al, Study of Acute Effects of Insulin–like Growth Factor I and II in Human Fat Cells, Journal of Clinical Endocrinology and Metabolism, vol. 65, pp. 732–737, 1987.

Brunette, D.M. Mechanical Stretching Increases the Number of Epithelial Cells Synthesizing DNA in Culture. J. Cell. Sci. 69:35, 1984.

Carter, D.R. Mechanical Loading History and Skeletal Biology. J. Biomechanics 20:1095, 1987.

Carter, D.R., Fyhrie, D.P. and Whalen, R.T. Trabecular Bone Density and Loading History: Regulation of Connective Tissue Biology by Mechanical Energy. J. Biomechanics 20:785, 1987.

Chamay, A. and Tschantz, P. Mechanical Influences In Bone Remodeling. Experimental Research On Wolff's Law Journal of Biomechanics 5:173, 1972.

Chisolm, E.M., Marr, S., Macfie, J., Broughton, A.C. and Brennan, T.G. Post–mastectomy breast reconstruction using the inflatable tissue expander. Br. J. Surg. 73:817, 1986.

Cohen, B.H. and Cosmetto, A.J. The Suture Tension Adjustment Reel. J. Dermatol. Surg. Oncol. 18:112, 1992.

Cohen, S.R., Rutrick, R.E., and Burstein, F.D. Distraction Osteogenesis of the Human Craniofacial Skeleton: Initial Experience with a New Distraction System. The Journal of Cranofacial Surgery 6:368, 1995.

Coleman, S.S. and Scott, S.M. The Present Attitude Toward the Biology and Technology of Limb Lengthening. Clinical Orthopaedics and Related Research 264:76, 1991.

Cong et al., Experimental Study of Microvascular Anastomosis Using a Dissolvable Stent Support in the Lumen Microsurgery, vol. 12, pp. 67–71, 1991.

Curtis, A.S.G. and Seehar, G.M. The control of cell division by tension or diffusion. Nature 274:52, 1978.

De Witt, M.T., Handley, C.J. Oakes, B.W., and Lowther D.A. In Vitro Response of Chondrocytes to Mechanical Loading The Effect of Short Term Mechanical Tension. Connective Tissue Research 12:97, 1984.

Didcott, C.C. and Schnaid, E. Treatment of flexion contractures of the knee joint with a slow continuous stretch apparatus. South African Journal of Surgery 26:173, 1988.

Finn, L.S., Saggers, G., Manders, E.K., and Rose, R.C. Soft Tissue Expansion to Elongate the Small Bowel. Surgical Forum 39:604, 1988.

Folkman, J. and Moscona, A. Role of cell shape in growth control. Nature 273:345, 1978.

Francis, A.J. and Marks, R. Skin Stretching and Epidermopoiesis, Br. J. exp. Path. 58:35, 1977.

Herzenberg, J.E., Davis, J.R., Paley, D., and Bhave, A. Mechanical Distraction for Treatment of Severe Knee Flexion Contractures. Clinical Orthopaedics and Related Research 301:80, 1994.

Hodgkinson, P.D. The Use of Skeletal Traction to Correct the Flexed Pip Joint in Dupuytren's Disease. Journal of Hand Surgery 19B:534, 1994.

Ilizarov, G.A. Clinical Application of the Tension–Stress Effect for Limb Lengthening. Clinical Orthopaedics and Related Research 250:8, 1990.

Ilizarov, G.A. The Tension–Stress Effect on the Genesis and Growth of Tissues: Part II The Influence of the Rate and Frequency of Distraction. Clinical Orthopaedics and Related Research 239:263, 1989.

Jain, M.K., Berg, R.A., and Tandon, G.P. Mechanical stress and cellular metabolism in living soft tissue composites. Biomaterials 11:465, 1990.

Johnson, T.M., Lowe, L., Brown, M.D., Sullivan, M.J., and Nelson, B.R. Histology and Physiology of Tissue Expansion. J. Dermatol. Surg. Oncol. 19:1074, 1993.

Kaiji et al., Microvascular Anastomosis Using Polyethylene Glycol 4000 and Fibrin Glue British Journal of Plastic Surgery, vol. 42, pp. 54–8, 1989.

Kim, K.H., Hong, C., and Futrell, J.W. Histomorphologic Changes in Expanded Skeletal Muscle in Rats. Plastic and Reconstructive Surgery 92:710, 1993.

Kimura, K. and Soper, R.T. A New Bowel Elongation Technique for the Short–Bowel Syndrome Using Isolated Bowel Segment Lowa Models. Journal of Pediatric Surgery 28:792, 1993.

Kirsch et al., A New Method for Microvascular Anastomosis: Report of Experimental and Clinical Research, The American Surgeon, vol. 12, No. 58, pp. 722–7, 1992.

Lorber, M. and Milobsky, S. Stretching of the Skin in vivo. A Method of Influencing Cell Division and Migration in the Rat Epidermis. The Journal of Investigative Dermatology 51:395, 1968.

Mackinnon, S.E. and Gruss, J.S. Soft tissue expanders in upper limb surgery. The Journal of Hand Surgery. 10A:749, 1985.

Manders, E.K., Schenden, M.J., Furrey, J.A., Hetzler, P.T., Davis, T.S. and Graham, W.P. Soft–Tissue Expansion: Concepts and Complications. Plastic and Reconstructive Surgery 74:493, 1984.

Marcus, J., Horan, D.B., and Robinson, J.K. Tissue expansion: past, present, and future. The Journal of the American Academy of Dermatology 23:813, 1990.

McCarthy, J.G., Schreiber, J., Karp, N., Thorne, C.H., and Grayson, B.H. Lengthening the Human Mandible by Gradual Distraction. Plastic and Reconstructive Surgery 89:1, 1992.

Mingli, Z., Dawei, W., and Lan, H. The Application of Skin External Expander to Postburn Advanced Scar Contracture. Plastic and Reconstructive Surgery 96:1600, 1995.

Moskovitz et al., Microvascular Anastomoses Utilizing New Intravascular Stents Ann Plat Surg, vol. 32, pp. 612–8, 1994.

Mustoe, T.A., Bartell, T.H. and Garner, W.L. Physical, Biochemical, Histologic, and Biomechanical Effects of Rapid versus Conventional Tissue Expansion. Plastic and Reconstructive Surgery 83:687, 1989.

Narayan, D., Castro, A., Jackson, I.T., and Herschman, B. Tissue expanders in the gut: a histological and angiographic study. J.R. Coll. Surg. Edinb. 37:402, 1992.

Olenius, M., Dalsgaard, C.J. and Wickman, M. Mitotic Activity in Expanded Human Skin. Plastic and Reconstructive Surgery 91:213, 1993.

Paley, D., Rumley, T.O., and Kovelman, H. The Ilizarov Technique: A Method to Regenerate Bone and Soft Tissue. Advanced Plast Reconstr Surg 7:1, 1991.

Rachmiel, A., Potparic, Z., Jackson, I.T. et al. Midface advancement by gradual distraction. British Journal of Plastic Surgery 46:201, 1993.

Rannels, D.E. Role of physical forces in compensatory growth of the lung. American Journal of Physiology 257:L179, 1989.

Rodriguez, E.K., Hoger, A., and McCulloch, A.D. Stress Dependent Finite Growth in Soft Elastic Tissues. J. Biomechanics 27:455, 1994.

Rosen, H.M. Facial Skeletal Expansion: Treatment Strategies and Rationale. Plastic and Reconstructive Surgery 89:798, 1992.

Russo, L.A., Rannels, S.R., Laslow, K.S., and Rannels, D.E. Stretch–related changes in lung cAMP after partial pneumonectomy. American Journal of Physiology: Endocrinology and Metabolism 20:E261, 1989.

Ryan, T.J. Biochemical consequences of mechanical forces generated by distention and distortion. J. Am. Acad. Dermatol 21:115, 1989.

Scheck, M. Translation of The Classic by Julius Wolff: Concerning the Interrelationship Between Form and Function of the Individual Parts of the Organism. Clinical Orthopaedics and Related Research 228:2, 1988.

Schmitz, et al., In Vivo Metabolic Action Of Insulin–Like Growth Factor I in Adult Rats, Diabetologia, 34:144–149, 1991.

Skoulis, T.G., Lovice, D., von Fricken, K., and Terzis, J.K. Nerve Expansion The Optimal Answer for the Short Nerve Gap. Behavioral Analysis. Clinical Orthopaedics and Related Research 314:84, 1995.

Slavin, S.A. and Colen, S.R. Sixty Consecutive Breast Reconstructions with the Inflatable Expander: A Critical Appraisal. Plastic and Reconstructive Surgery. 86:910, 1990.

Smith et al., Insulin–Like Growth Factor–I Is an Essential Regulator of the Differentiation of 3T3–L1 Apidocytes, The Journal of Biological Chemistry, vol. 263, No. 19, pp. 9402–9408, Jul. 5, 1988.

Squier, C.A. The Stretching of Mouse Skin in Vivo: Effects on Epidermal Proliferation and Thickness. The Journal of Investigative Dermatology 74:68, 1980.

Stark, G.B., Dorer, A., Walgenbach, K.J., Grunwald, F., and Jaeger K. The creation of a small bowel pouch by tissue expansion–an experimental study in pigs. Langenbecks Archive for Chirurgie 375:145, 1990.

Stricker, S.J. Ilizarov Lengthening of a Posttraumatic Below Elbow Amputation Stump. Clinical Orthopaedics and Related Research 306:124, 1994.

Sugihara, T., Kawashima, K., Igawa, H., Ohura, T., Yamamura, M., and Ohata, N. Mandibular lengthening by gradual distraction in humans. European Journal of Plastic Surgery 18:7, 1995.

Sumpio, B.E., Banes, A.J., Link, W.G., and Johnson, G., Jr. Enhanced Collagen Production by Smooth Muscle Cells During Repetitive Mechanical Stretching. Arch. Surg. 123:1233, 1988.

Urschel, J.D., Scott, P.G. and Williams, H.T.G. The effect of mechanical stress on soft and hard tissue repair; a review. British Journal of Plastic Surgery 41:182, 1988.

Vandenburgh, H. and Kaufman, S. In vitro Model for Stretch–Induced Hypertrophy of Skeletal Muscle. Science 203:265, 1979.

Vandenburgh, H.H. Mechanical forces and their second messengers in stimulating cell growth in vitro. American Journal of Physiology 262:R350, 1992.

Versaci, A.D. Reconstruction of a Pendulous Breast Utilizing a Tissue Expander. Clinics in Plastic Surgery 14:499, 1987.

Villa, A., Paley, D., Catagni, M.A., Bell, D., and Cattaneo, R. Lengthening of the Forearm by the Ilizarov Technique. Clinical Orthopaedics and Related Research 250:125, 1990.

Volkov, M.V. and Oganesian, O.V. Restoration of Function in the Knee and Elbow with a Hinge–Distractor Apparatus. The Journal of Bone and Joint Surgery 57A:591, 1975.

Watson, P.A. Function follows form: generation of intracellular signals by cell deformation. FASEB J. 5:2013, 1991.

Wei et al., The Temporary Stent Technique: An Easier Method of Micro–Venous Anastomosis British Journal of Plastic Surgery, vol. 42, pp. 54–8, 1989.

Wilson, E., Mai, Q., Sudhir, K., Weiss, R.H. and Ives, H.E. Mechanical Strain Induces Growth of Vascular Smooth Muscle Cells via Autocrine Action of PDGF. Journal of Cell Biology 123:741, 1993.

Wood, R.J., Adson, M.H., VanBeek, A.L., Peltier, G.L., Zubkoff, M.M., and Bubrick, M.P., Controlled Expansion of Peripheral Nerves: Comparison of Nerve Grafting and Nerve Expansion/Repair for Canine Sciatic Nerve Defects. The Journal of Trauma 31:686, 1991.

Vandenburgh, H.H. Motion into mass: how does tension stimulate muscle growth? Medicine and Science in Sports and Exercise 19:S142, 1987.

* cited by examiner

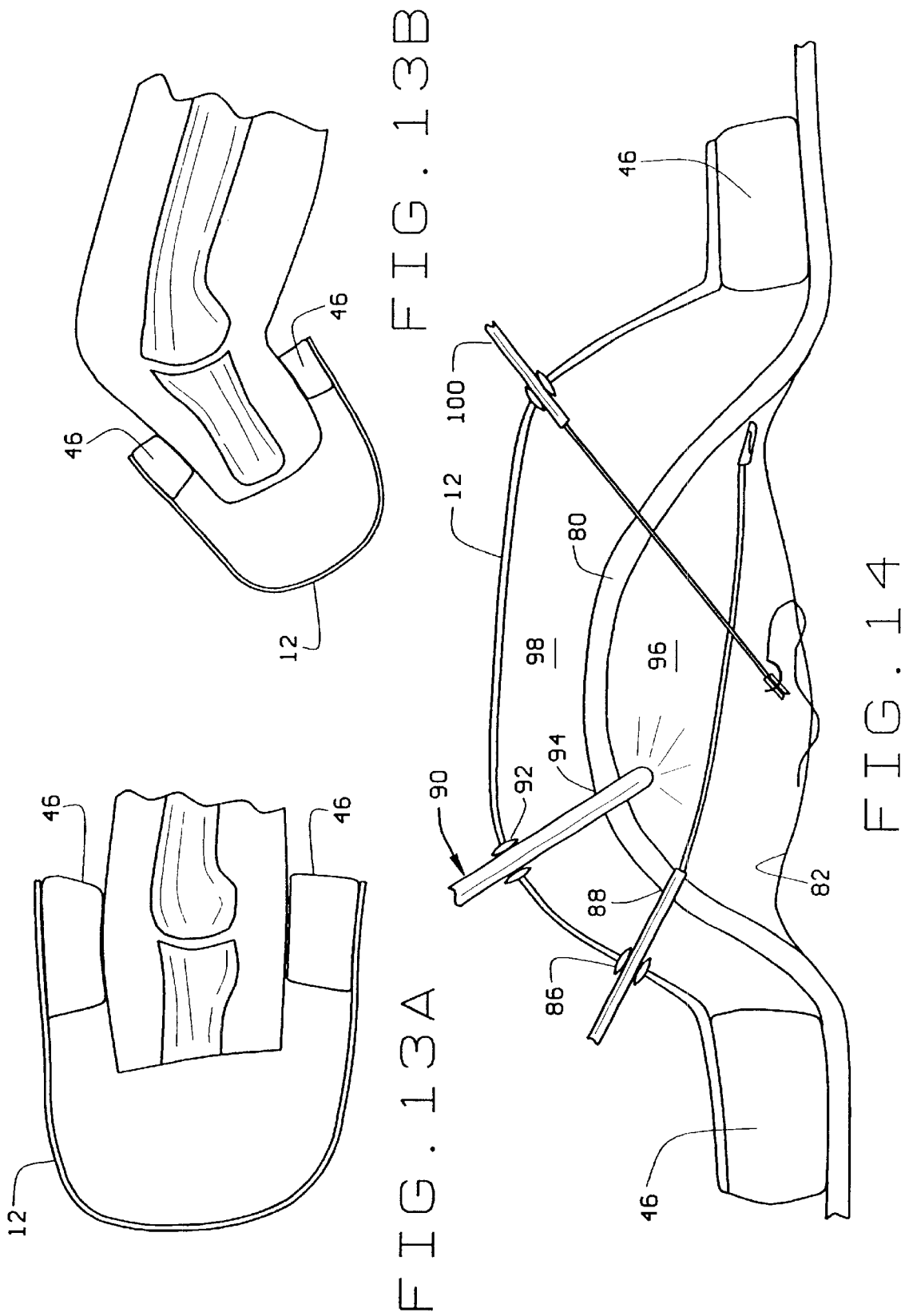

VACUUM DOME WITH SUPPORTING RIM AND RIM CUSHION

This application is a continuation of Ser. No. 08/698,941 filed Aug. 16, 1996 now ABN; which is a continuation-in-part of U.S. patent application Ser. No. 08/516,623 filed Aug. 18, 1995 now U.S. Pat. No. 5,676,634, entitled "Method And Apparatus For Soft Tissue Enlargement With Balanced Force Appliance", which is a continuation-in-part of a U.S. patent application Ser. No. 08/504,640 filed Jul. 20, 1995 now U.S. Pat. No 5,695,445, entitled "Method And Apparatus For Soft Tissue Enlargement By Distractive Force", which is a continuation of U.S. patent application Ser. No. 08/220,186 filed Mar. 30, 1994 now U.S. Pat. No. 5,536,233 entitled "Method And Apparatus For Soft Tissue Enlargement".

BACKGROUND AND SUMMARY OF THE INVENTION

There are numerous instances where persons desire enlargement of the soft tissues in their bodies. One such instance is for the replacement of one or both breasts amputated during a mastectomy in order to restore physiological symmetry and psychological well-being. Other instances are for correction of natural abnormalities such as dimpling. Still other instances are for augmentation of physical attributes to improve cosmetics and self-esteem. These latter soft tissue enlargements are principally directed to breast enlargement in females and penis enlargement in males.

Prosthetic implants have been developed for insertion below the skin. However, the severity of the potential complications including scarring, implant rupture, capsular contracture, necrosis and implant migration as well as the recent adverse publicity thereof have significantly reduced the desirability of these implants. Thus, there is a societal need for other means to obtain soft tissue enlargement.

Some soft tissue enlargements occur naturally. For instance, during pregnancy, the skin over a woman's abdominal region enlarges approximately nine times its previous area to accommodate the fetus without a proportional decrease in skin thickness. In other words, the abdominal skin tissue actually enlarges and does not merely stretch during pregnancy. Similarly, the skin will expand to accommodate any growth under the skin.

In the past, plastic surgeons have used this phenomenon to their advantage to expand skin in order to accommodate prosthetic implants. To conduct this procedure, the surgeon inserts a balloon beneath the skin in the area where additional skin is desired. By progressively expanding the balloon, the skin first stretches and eventually actually grows to accommodate the increased volume underneath it. When the desired amount of skin is formed, the balloon is deflated and removed, and the implant is inserted into the cavity left by the balloon. Similar methods have been used by native African tribes to enlarge lips, nostrils, and earlobes.

Other surgical techniques have used tissue expansion to achieve other types of soft tissue growth. For instance, balloons have been successfully expanded underneath nerves, veins, tendons, and the like to thereby elongate these tissues to repair damage and alleviate various abnormalities.

A more advanced surgical method is known as callotasis or limb lengthening. This method comprises cutting the bone about its periphery at the location where lengthening is desired, leaving the tissues inside and around the bone intact. Brackets are attached to the bone on each side of the separation, and the bone segments are slowly pulled away from one another while remaining integral over a period of several months. Not only does this cause the mended bone to be longer, but also the soft tissue surrounding the bone actually grows to accommodate the increased limb length. Similar methods have been used by African native tribes to lengthen necks for cosmetic purposes.

Each of these above-mentioned apparatuses and methods requires an invasive surgical technique to accomplish the soft tissue expansion. Invasive techniques increase the likelihood of the complications associated with the procedure including those mentioned above with respect to implant surgery. In addition, the expense of surgery precludes many persons from having their abnormalities corrected or physical attributes enhanced.

Other soft tissue enlargement techniques have been developed which use other mechanisms to cause the enlargement. For instance, an instrument and technique have been developed for the non-surgical correction of inverted nipples due to short lactiferous ducts. The instrument is comprised of a cup having an internal volume shaped like that of the final desired nipple. The user places the cup over the inverted nipple, pumps the air out of the cup with a syringe and adjusts the vacuum within the cup using a check valve to just below the threshold of discomfort. Thus attached, the device puts he lactiferous ducts in tension and extends them sufficiently after two to three months of wear at 8–12 hours per day.

Although this device is sufficient for its intended purpose, it is not suitable for general soft tissue enlargement. Laceration and contusion can occur if too strong of a suction is applied to soft tissue. As the pressure within the inverted nipple instrument is not regulated, contusion or laceration can occur. When a vacuum is developed within the cup of the instrument, an equal and opposite force is applied to the patient about the rim of the cup. Excessive contact forces against the patient can cause ulceration, laceration, and contusions. As the contact forces are not regulated in the nipple instrument, these further complications also can occur. In addition, general soft tissue enlargement is not feasible with the instrument due to the size and shape of the cup.

Another prior art device is disclosed in U.S. Pat. No. 936,434 as a device for enlarging a woman's breasts. This device included a pair of cups for placement on the breasts and a pump for exhausting the air from between the cups and breasts. However, this patent provides no teaching as to the pressures to be used, the potential danger to the skin tissues, or any suggestions as to how the device is to be retained in place during use. Apparently, the device is used in a clinical setting and is not suitable for long term wear such as for 8–10 hours. As the patent suggests that the vacuum acts to cause the veins and arteries to engorge, thereby nourishing the breasts, it is clear that the patentee is suggesting that the breast tissue actually expands through this expansion of blood vessels alone. This patent has been the subject of ridicule by at least one medical authority. See "An Anthology Of Plastic Surgery" edited by Harry Hayes, Jr., M.D., Section 6, "Quackery and Nostrums" pub. 1986 by Aspen Publishers, Rockville, Md.

Another prior art device although notorious is worthy of note. This device is commonly referred to as a penis pump and is sold primarily as a novelty as its long-term enlargement efficacy has never been proven and is in fact universally disclaimed by its distributors. The device is comprised of a cylinder having one open end into which the penis is inserted and a pump attached to it such that a vacuum can be created within the cylinder. Not only does this device have the same drawbacks as the nipple instrument with respect to potential complications, but also it is unlikely that sufficient vacuum can be maintained by the device to cause any notable long-term soft tissue enlargement. Further, this device is apparently designed to accomplish two tasks unrelated to enlargement. First, the device is used for stimulation and sexual gratification. Second, the device is used to promote erection by drawing blood into the penis.

Most of these prior art devices and methods have failed to achieve long term soft tissue enlargement while preventing damage to the soft tissue being enlarged, as well as surrounding tissue. As disclosed and claimed in the parent applications noted above, the inventor herein has succeeded in designing and developing a new generalized method and apparatus for soft tissue enlargement which prevents damage to soft tissue. The apparatus used for this enlargement is comprised of a rigid, fluid-impervious dome having a rim about its periphery and a vacuum pump for reducing pressure within the dome. The rim has sufficient surface area such that the pressure applied to the patient by the rim is less than or equal to the negative pressure applied to the soft tissue under the dome. In the parent applications, one specific teaching to achieve this balanced force utilized a rim with substantially the same cross-sectional area as the normal area of the dome. Thus, as long as pressure within the dome is regulated to a limit below which medical complications will not occur, the opposing contact pressure against the patient is below this threshold as well. With this approach, damage is avoided not only to the soft tissue being enlarged, but the surrounding tissue as well. In the preferred embodiment of the apparatus, the vacuum pump has a self-contained power source. In addition, a pressure sensor and servomechanism control the pump such that the vacuum within the dome is maintained at a magnitude less than 35 mmHg. Variant embodiments may be configured to fit over and enlarge a human breast, a human penis, or any other desired area.

In still another patent application filed on behalf of the present inventor entitled "Method And Apparatus For Promoting Soft Tissue Enlargement and Wound Healing" having Ser. No. 08/408,423 filed Mar. 22, 1995, the present inventor disclosed and claimed an invention which utilizes a rigid fluid-impervious dome having a rim about its periphery and a vacuum pump for reducing pressure to thereby apply a distracting force to the soft tissue isolated by and within the dome. The dome may be conveniently located over an open wound in order to promote healing of the wound by enlarging the soft tissue under the dome. As the soft tissue grows, it promotes healing of the wound through acceleration of the closing thereof by soft tissue growth. As wounds may be received by a patient to any part of his body, the inventor's prior disclosed and claimed invention includes the use of a dome over virtually any part of the human body.

In implementing these prior inventions, the inventor intends that it be capable of achieving its therapeutic effect without creating any long term tissue necrosis from use. In other words, a vacuum must be applied to the desired area to achieve the therapeutic effect for sufficient periods of time without applying too great a vacuum or contact pressure which will damage the underlying tissue. As considered from this generalized approach, one of ordinary skill in the art would understand the inventor's teaching to include the idea of providing a smaller vacuum pressure within the dome and balancing that smaller vacuum with a rim having a surface area less than the normal area of the dome, thereby creating a greater contact pressure which is still within acceptable limits. Still another approach which may very well provide a therapeutic effect would be to cycle the vacuum in the dome such that it is applied for periods of time at elevated levels and relaxed levels so that the rim might also have a cross-sectional area less than the normal area of the dome, but yet avoid creating any tissue necrosis. The cycling of the vacuum pressure in the dome could be readily achieved in an automatic manner by appropriately programming the vacuum pump and regulator. Therefore, the invention should be understood as being limited only by the current medical understanding of the causative effects of pressure sores and other tissue damage by an applied pressure or vacuum.

It is well recognized in the medical literature that decubitus ulcers are caused by unrelieved external pressure that occludes blood flow and results in tissue necrosis. In recognition of this fact, these ulcers are called pressure sores. The average capillary pressure in human skin is around 15–20 mmHg. E. M. Landis, *Micro-Injection Studies of Capillary Blood Pressure in Human Skin,* 15 Heart 209–228, (1930). For convenience, 20 mmHg will be used to describe this pressure throughout the remainder of this description. However, it should be understood that pressures below 20 mmHg may also be used without departing from the scope of this invention and that these lower pressures may provide additional margins in preventing damage to tissues. Therefore, the local application of an external pressure up to 20 mmHg will not collapse capillaries adjacent the location of the applied pressure and thus will not disturb the circulation. Therefore, local application of contact pressures less than or equal to 20 mmHg are well tolerated for prolonged periods of time. This tolerance has been confirmed by the inventor through use of a prototype which did not cause adverse effects after many hours of continuous use as long as the pressure under the rim remained below or around 20 mmHg.

Pressures greater than 20 mmHg will occlude the capillaries and stop tissue perfusion. Tissues can tolerate short periods of ischemia, but if the pressure is continuous and perfusion is not restored within a relatively short period of time, tissue damage will ensue. "The time factor is thus more important than pressure intensity". A pressure of 100 mmHg will lead to pathologic changes after only two hours. T. Hussain, *An Experimental Study of Some Pressure Effects on Tissues, with Reference to the Bed-Sore Problem,* 66 J. Path. Bact. 347–358, (1953).

The experimental results of additional investigators can be used to develop a safe time-pressure curve above which tissue damage will ensue. For instance, 20 mmHg is well tolerated for prolonged periods of time, but 40 mmHg will lead to tissue injury if the pressure is not relieved for 13 hours. The injury is more severe if the pressure is 60 mmHg, and even greater injury will result with a pressure of 100 mmHg after shorter periods of time. O. Lindan, *Etiology of Decubitus Ulcers: An Experimental Study,* 42 Arch. Phys. Med. Rehab. 774–783, (1961). Similarly, a pressure of 70 mmHg, if unrelieved, will lead to pathologic changes after 2 hours. However, if the pressure is intermittent, applied 5 minutes on, and 5 minutes off, there is no pathologic tissue changes. M. Kosiak, *Etioloqy of Decubitus Ulcers,* 42 Arch. Phys. Med. Rehab. 19–29, (1961).

These findings are consistent with the clinical testing of the prototype of the breast device. It was found that a continuous pressure under the rim of 40 mmHg could be tolerated for only one hour by healthy volunteers. After one hour, the volunteers started to complain of pain which is the warning sign of impending tissue damage. Higher pressures led to pain under the rim after even shorter periods of time. Lower pressures around 30 mmHg led to pain after 4 hours. However, if the pressure is allowed to cycle, that is if it is dropped down to 0–20 mmHg to allow the tissues to temporarily reperfuse for a few minutes, higher peak pressures can be tolerated. The higher the peak pressures, the shorter they are tolerated and the longer the low pressure part of the cycle needs to be to allow the tissues to recuperate.

Therefore, pressures under the rim greater than 20 mmHg can only be tolerated if there is a means to continuously cycle the pressure peaks on and off allowing for tissue re-perfusion during the off periods. The higher the peaks, the shorter the pressures are tolerated and the longer the period of low pressure recuperation needs to be.

From the above experimental animal data and human study, the inventor concludes that 20 mmHg is the highest pressure that can be safely tolerated under the rim on a prolonged basis. Higher pressures can only be applied intermittently, and then cycled down to less than 20 mmHg.

The method of use is comprised of the steps of attaching the dome to the location of desired enlargement, and creating a vacuum within the dome. In the continuous application method in which the vacuum is applied at pressures that can be withstood continuously, the vacuum should be maintained for a minimum of eight hours per day and results should be sufficient after several months.

As indicated by the summary of the medical literature given above, a vacuum dome may also be used in alternative methods in keeping within the scope of the inventor's concept. For example, the device might have a rim cross-sectional area substantially less than the normal area of the dome and be used in either of two methods. In a first method, a somewhat lower vacuum pressure may be induced in the dome such that the opposing contact pressure under the rim may be maintained at bearable pressures for extended periods of time and yet provide a therapeutic effect. Alternatively, the vacuum in the dome may be regulated in a routine which provides somewhat higher vacuum pressures in the dome for shortened periods of time separated by periods of lower vacuum pressures to allow tissue reperfusion. In other words, alternating cycles of high vacuum, tissue reperfusion, high vacuum, tissue reperfusion, etc., may achieve a therapeutic effect in enlarging the soft tissues. With either of these methods, the rim may have a cross-sectional area substantially less than the normal area of the dome.

In an alternate embodiment, the dome may include a flexible sheet attached about the rim and spanning the dome. The sheet may be applied to the desired soft tissue with an adhesive, and the vacuum may be applied between the dome and the sheet to introduce a tensile force to the surface of the soft tissue so as to pull the soft tissue away from the body. The adhesive may comprise typical adhesives or glues, as well as, sticky gels or sheets of double-sided adhesive tapes. Further, the adhesive may be an adhesive substance embedded in the sheet or in the rim of the dome.

In addition to the embodiments already discussed, the inventor has conceived of additional embodiments which further utilize the vacuum dome. One such embodiment is especially useful in the healing or reconstruction of amputation stumps. Whether the amputation is exemplified by an acute open wound (e.g. fingertip amputations) or an extremity amputation stump that tends to break down because of a deficiency in soft tissue padding, the growing of soft tissue may be especially advantageous in healing these wounds and adding tissue padding to what might otherwise become a chronic wound particularly susceptible to infection. In this application, the vacuum dome is supported around the amputation stump, much as taught in the inventor's prior disclosures, and maintained using an appropriate protocol to encourage the growth of soft tissue. Still another newly conceived application for the vacuum dome is as an aid in endoscopic or other minimally invasive surgery. In this application, a vacuum dome may be placed over a skin surface and used as an external retractor to lift up the surface integument to thereby create an optical cavity for subcutaneous endoscopic surgery. A pressure differential introduced within the dome may be used to separate the skin from the underlying tissue without interfering with either surgical access or viewing by the surgeon during the procedure. As such, this application for the vacuum dome provides distinctive advantage over several of the prior art approaches including the use of balloons to gently separate the skin from the underlying tissue. When in place, the balloon obviously interferes with surgical access and obscures surgical viewing. Applying a vacuum to the skin to encourage its separation may be done externally and thereby leave clear access in sight to the surgical point of contact.

In implementing any of the embodiments of these prior inventions, the inventor utilizes a dome which is positioned adjacent a skin surface and which requires an airtight seal between the dome and the skin surface. In several of these embodiments, a vacuum may be drawn within the dome as well. In utilizing this construction, the inventor is aware of potential complications which can develop when an area of the body needs to be enclosed for prolonged periods of time within the dome having an airtight seal. For example, while a rim made of conforming or other soft materials may suffice for temporary use, a number of problems arise in the skin contact area when prolonged negative pressure application is necessary. The present invention includes in its various aspects various features which are intended to deal with these problems.

One such concern is for the management of the shear forces generated by the dynamic inward pull of the skin. As explained above, drawing a vacuum within the dome creates dynamic forces under the rim of the dome as the skin and other soft tissue is "pulled" up into the dome by the vacuum. Generally speaking, these forces place a shear force on the skin which has been found to be roughly equivalent to a normal force in that the skin blood flow decreased roughly linearly with the increase of shear forces. See the effect of shear forces externally applied to skin surface on underlying tissues by Zhang and Roberts, *Journal of Biomedical Engineering*, Vol. 15, No. 1, January 1993, pages 451–456. The effect of these shear forces may be dramatically minimized by providing an interface between the dome and the skin which allows inward displacement of the contact surface in response to the vacuum. There are numerous examples of structures which could achieve this desired inward displacement including a gel, an inflatable bladder, a bellows, a corrugated collapsible structure, or virtually any other mechanical/geometrical design which will allow substantially inward concentric movement of the contact surface area.

Still another problem encountered in applying a dome to a skin surface is the possibility for tissue damage at points of pressure concentration. It is well known from the literature on pressure sores that the body has numerous pressure points where bony prominences lack the thick layer of soft tissue padding needed to dissipate the pressure subjected to the overlying skin. These are the prominences where pressure sores tend to develop. Furthermore, with movement of the body parts, these pressure points are not static and fixed but have a tendency to shift from one cutaneous area to the other. To avoid creating points of pressure concentration at these shifting surfaces over bony prominences, it is important for the cushion under the dome to be able to constantly and evenly distribute the pressure on its underlying skin. This even distribution may be provided by a rim on the dome that has fluid-like properties. This cushion could be constructed with an air or fluid bladder, or any other type of membrane containing a gel-like fluid. Still other equivalent structures could be envisioned to achieve the same effect such as the use of a gel-like substance that can retain its contour and shape without a membrane layer boundary. This gel-like substance would approximate the hydraulic effect of a fluid-filled bladder.

A related problem to that of shifting points of pressure concentration is the overall contour of the body surface underlying the rim. This is especially the case as a wearer of the dome performs his routine daily activities. These routine daily activities would ordinarily shift the dome and would potentially cause the dome rim to contact other areas of the body not having the same contour as at the "at rest" orientation. For these reasons, the rim should be designed to constantly accommodate a potentially ever-changing contour for the underlying body surface. To achieve this, the rim should be flexible and have a surface with mechanical bending properties approximating those of the underlying body tissue. This may be achieved by using a cushion having the fluid-like properties as described above to accommodate pressure concentration caused by bony prominences.

Another significant consideration in utilizing a dome in the various inventions developed by the inventor herein is the requirement that an airtight seal be maintained to preserve minimal to small vacuum pressure differentials. Escaping air at the interface between the rim and the skin leads to loss of vacuum and necessitates frequent activation of a pressure pump. This is undesirable in that it is at best a nuisance. Loss of vacuum is untenable for a truly portable device which would require a portable pump and power supply. In any event, the integrity of the seal between the rim and the skin directly impacts on the useability and performance of the vacuum dome. Ideally, a cushion may be utilized under the rim and between it and the skin to provide an airtight seal without an excessive force being applied as excessive forces may themselves create tissue damage. A heightened seal integrity may be achieved through the use of a "sticky" material which may be placed under the cushion or surrounding the cushion so as to adhere and bond to the skin a surface which preserves the pressure integrity. This "sticky" aspect of the present invention may be achieved by utilizing a material for the cushion itself which has a sticky, gooey, gluey, or gummy surface property. Numerous materials including polymers such as silicone, hydrogels, and many other low durometer synthetic rubbers and gels have this inherent surface property. A sheet or layer of this "sticky" polymer or other material may be added as a skin surface contact sole to the undersurface of the cushion for the rim, with the cushion itself not exhibiting this "sticky" property. Still another alternative is a skin adhesive layer which can be painted, sprayed, or otherwise applied to the lower surface of the cushion intended to contact the patient's skin. Again, this would essentially form a "sole" for the rim cushion. Still another methodology may consist of applying a layer of adhesive by painting, spraying, or otherwise adhering a gluey or sticky surface directly to the skin itself. A "sticky" tape may be used as the sole or even a double-sided sticky skin tape can be provided to interface between the rim cushion and the skin. Those of ordinary skill in the art could conceive of other ways to achieve this "sticky" contact between the dome and the underlying skin in order to maintain the integrity of the seal. Furthermore, the combination of the relatively hard rim that can distribute the counter-pressures evenly along its width with the underlying cushion of gel or fluid-filled bladder when combined with the adhesive "sticky" sole for maintaining the integrity of an airtight seal can be blurred and yet be covered by the inventor's inventive concepts. For example, these advantages may all be achieved through structure constructed out of the same material with a gradient of tackiness or durometer properties.

While the practical advantages and features of the present invention and method have been briefly described above, a greater understanding of the novel and unique features of the invention may be obtained by referring to the drawings and Detailed Description of the Preferred embodiment which follow.

BRIEF DESCRIPTION OF THE DRAWINGS

FIGS. 13A and 13B depict the application of the dome to an amputated stump of either a fresh amputation or an amputation having deficient soft tissue;

FIG. 14 depicts the vacuum dome applied over a skin flap and adapted for endoscopic surgery to assist in separating a skin flap from the underlying musculature;

DETAILED DESCRIPTION OF THE PREFERRED EMBODIMENT

Figure 1:
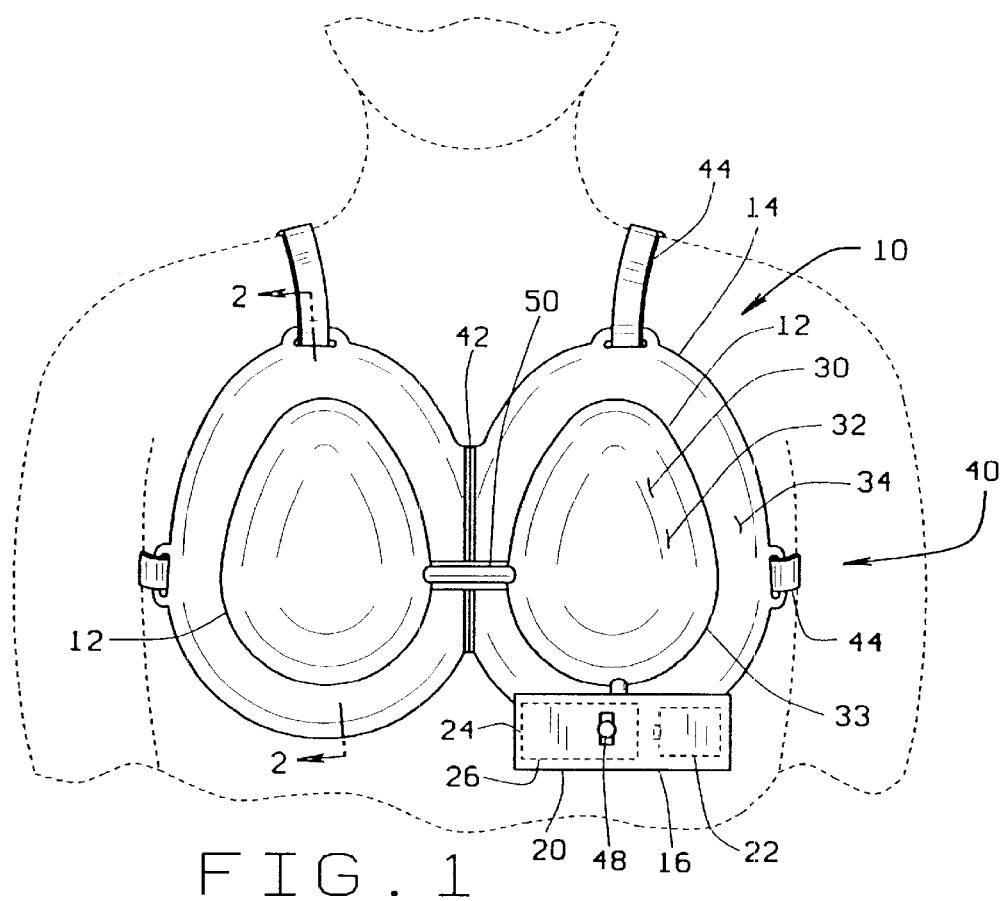
FIG. 1 is a front elevation view of the soft tissue enlargement apparatus, showing the breast augmentation embodiment.

One embodiment of the soft tissue enlargement apparatus 10 is generally comprised of a dome 12 having a rim 14 and a vacuum pump assembly 16 for creating a vacuum within the dome. Although the vacuum pump assembly 16 may be a separate hand-held pump in one variant embodiment, in the preferred embodiment the vacuum pump assembly 16 is a self-contained vacuum pump 20 with an independent power source 22, pressure sensor 24, and servomechanism 26 for driving, regulating and controlling the vacuum pump 20.

Regulation of the vacuum within the dome is essential to prevent contusions caused by rupturing capillaries adjacent the surface of the skin. Medical data suggest that these contusions will not occur if vacuum within the dome is maintained at less than 20 mmHg. Thus, the vacuum pump 20 must be regulated to control the vacuum within the dome to within this limit. In addition, skin ulceration can occur if excessive contact pressures are applied thereto. Medical data suggest that a contact pressure less than 20 mmHg may be applied indefinitely without such ulceration. However, contusions may occur due to positive contact pressures upon the skin at pressures above this ulceration limit. The preferred embodiment of the present invention was developed with these limits in mind and will not apply a vacuum greater than 20 mmHg or constant contact pressure greater than 20 mmHg.

Several forces are developed within the dome and about the rim as a result of evacuating air from the dome. A suction or tensile force $F_s$ is developed within the dome 12 equal to the vacuum pressure $P_1$ multiplied by the enclosed tissue surface area 30, $A_s$. The vector sum of the tensile force upon the tissue surface area 30 may be called the normal force $F_1$ and is equal to the vacuum pressure multiplied by the normal area 32, $A_1$ of the dome opening, i.e., the projected area bounded by the periphery 33, or $F_1=P_1A_1$. An opposing force $F_2$ is imposed on the user by the rim 14 to balance the normal force $F_1$ and is equal but opposite to the normal force. The contact pressure $P_2$ of the rim 14 against the user is equal to this opposing force $F_2$ divided by the annular rim surface area 34, $A_2$, i.e., $P_2=F_2/A_2$ or $F_2=P_2A_2$. As the magnitude of the opposing force is equal to the magnitude of the formal force, $F_1=F_2$ and $P_1A_1=P_2A_2$. Therefore, if the rim surface area 34, $A_2$ is configured to be greater than or equal to the normal area 32, $A_1$ at the dome opening, then the contact pressure against the patient's skin will not exceed the magnitude of the vacuum within the dome 12, i.e., $P_2=P_1$. Similarly, the rim surface area 34, $A_2$ may be sized with respect to the normal area 32, $A_1$ so that the contact pressure $P_2$ is maintained below 20 mmHg when the vacuum pressure $P_1$ within the dome is maintained at less than 20 mmHg. Likewise, if the vacuum pressure is cycled, different area ratios may be used to optimize the therapeutic effects while minimizing the potential for damage to the soft tissue within the dome or beneath the rim.

Figure 3:
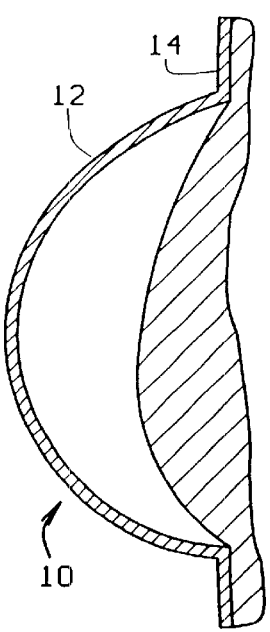
FIG. 3 is a cross-sectional schematic of a dome and soft tissue in the early stages of enlargement.
Figure 4:
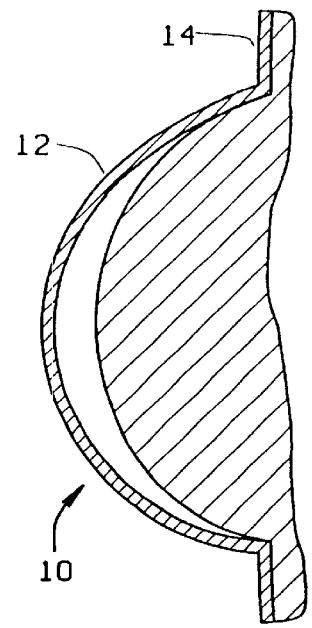
FIG. 4 is a cross-sectional schematic of a dome and soft tissue in the latter stages of enlargement.

As the soft tissue enlarges, the rate of enlargement increases due to a beneficial physical phenomenon. If the tissue only slightly protrudes into the dome as shown in FIG. 3 and as is typically the initial condition, then the surface area 30 under the dome is only slightly larger than the normal area 32 at the dome opening. Therefore, the vacuum pressure $P_1$ acts on a surface area 30 which approaches the minimal value of the normal area. As enlargement occurs, more tissue protrudes into the dome 12 as shown in FIG. 4 thereby providing more surface area 30 under the dome. Because the surface area 30 under the dome is larger, the area over which the vacuum pressure acts is larger. For a given pressure, the enlargement of the soft tissue is a function of the surface area. Therefore, the total rate of enlargement of the soft tissue increases as treatment continues because the surface area under the dome is ever increasing. In other words, with more tissue under the dome the tensile force $F_s$ is greater ($F_s=PA_s$) and the breast grows larger faster. This however has no effect on the opposing force, or for that matter the normal force, as the tensile force $F_s$ is a vector which must always sum into the normal force. In still other words, a unit of surface area enlarges at a constant rate for any given pressure, but as the soft tissue surface area under the dome increases, there are more units of surface area increasing at the constant rate. Therefore, the total rate of enlargement increases as treatment continues even though the vacuum pressure is not increased.

Figure 2:
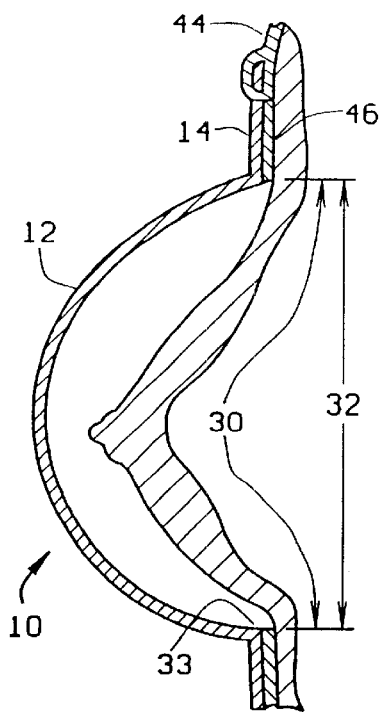
FIG. 2 is a cross-sectional view of the breast enlargement embodiment taken in the plane of line 2—2 of FIG. 1.

One specific embodiment includes a dome 12 configured to fit over a human breast as shown in FIGS. 1 and 2. This embodiment includes a rim 14 having a surface area 34 approximately equal to the normal area 32 of the dome opening thereby preventing medical complications to the soft tissue as long as the pressure is properly regulated within the dome 12. However, alternate embodiments having a rim 14 with a surface area 34 equal to or less than the normal area 32 of the dome opening may be used depending upon the amplitude of the vacuum pressure used and depending upon whether the vacuum pressure is constant or varied. The pressure reducing means 16 is located underneath the patient's breast, so that the apparatus 10 may be hidden under loose-fitting clothes. As with the general embodiment, the vacuum pump assembly 16 of this embodiment is preferably comprised of a vacuum pump 20 with a power source 22, a pressure sensor 24 and servomechanism 26 to drive and control the vacuum pump and to regulate the pressure within the dome 12.

As shown in FIG. 1, this specific embodiment may take the form of a bra 40 having two domes 12 spaced by a hinge 42. Straps 44 may be attached to the bra 40 to retain the bra 40 in place. A gasket 46 may also be included about the rim 14 to improve the patient's comfort and enhance the seal about the rim. In the preferred embodiment, this gasket 46 may be a silicone gel cushion or other soft, conforming type material. Petroleum jelly may also be used to supplement or supplant the gasket. A manual override 48 is included on the vacuum pump assembly 16 so that the patient or doctor may vary the pressure below the optimal level so as to be more comfortable. Although two vacuum pump assemblies 16 may be used, one depending from each dome 12 so as to provide different pressures in the domes, the preferred embodiment places the domes in fluid communication with a conduit 50. Two pump assemblies 16 may be desired to balance the size of two breasts as they are enlarged, as many women have differently sized breasts. Further, the pump may be replaced with a manually actuated pump such as a bulb-type pump.

Figure 5:
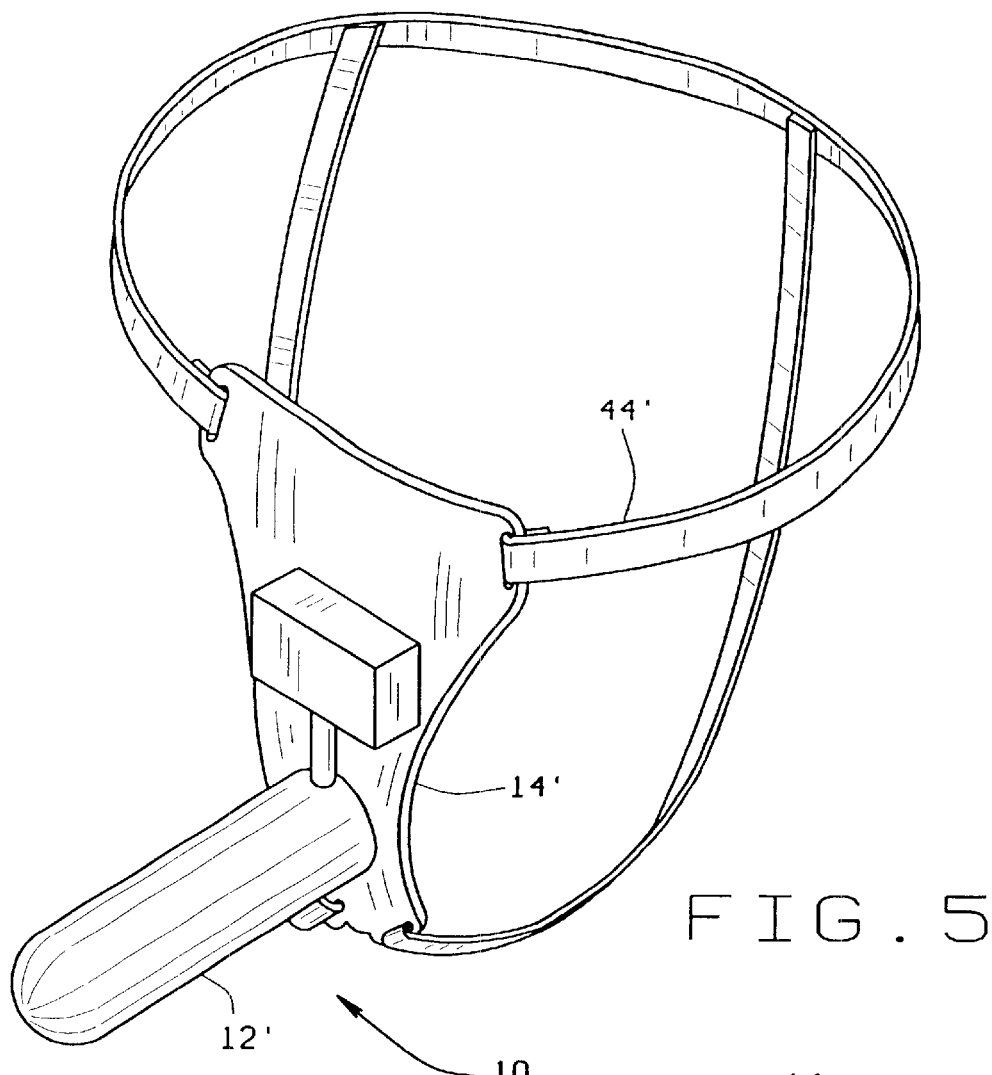
FIG. 5 is an orthographic projection of the penile augmentation embodiment of the present invention.

A second specific embodiment is shown in FIG. 5 wherein the dome 12 is configured to fit over a human penis. As can be seen from the figure, this embodiment comprises essentially the same features as the bra embodiment described above. The principal differences between these embodiments are the configurations of the dome 12' and rim 14' as well as the positioning of the straps 44'.

Figure 6:
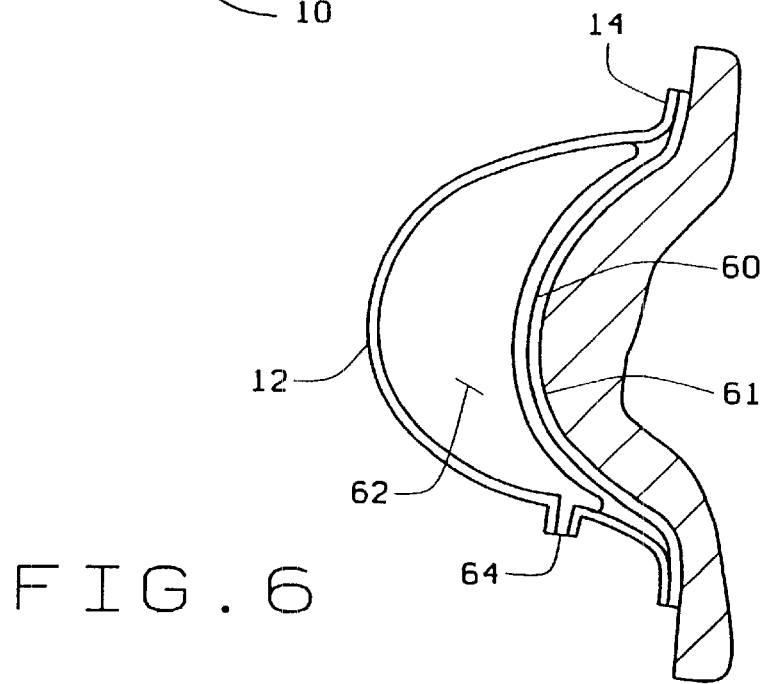
FIG. 6 is a cross-sectional schematic of a fourth alternate embodiment wherein a flexible sheet which may be bonded to the soft tissue spans the rigid dome to prevent leakage between the dome and the skin.
Figure 7:
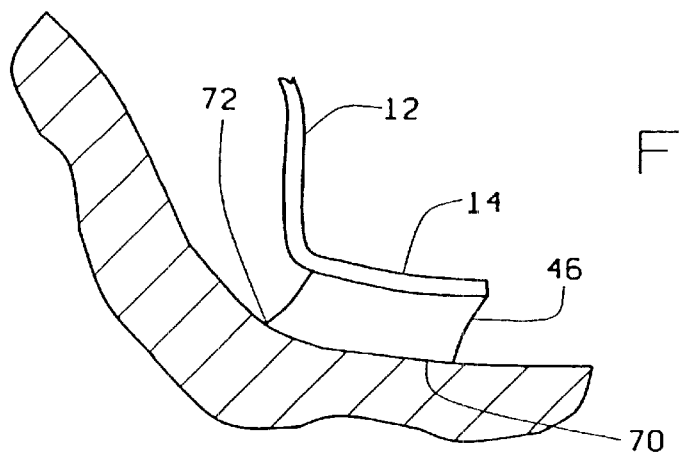
FIG. 7 is a cross-sectional diagram of an alternate embodiment wherein a flexible rim gasket is used to distribute the forces along the rim.

Another alternate embodiment is shown in FIG. 6. In this embodiment, a sheet of material 60 is adhesively applied to the desired soft tissue using double-sided tape or other temporary adhesive 61. The sheet 60 is attached to the rim 14 so that a hermetic seal is formed between the sheet and the dome 12. The cavity 62 between the dome 12 and sheet 60 may be evacuated as in the first general embodiment through a port 64 to apply the tensile force to the soft tissue. This embodiment eliminates the potential for leakage between the rim 14 and the skin adjacent the rim by permitting the user to adhesively bond the sheet 60 to the soft tissue mass and to evacuate the cavity 62 to apply the tensile force. The adhesive 61 may comprise typical adhesives or glues, as well as, sticky gels or sheets of double-sided adhesive tapes. Further, the adhesive 61 may be an adhesive substance embedded in the sheet 60. The double-sided tape or other adhesive means 61 makes attachment more convenient as the tape may be removed from the flexible sheet 60 after each use and disposed. A new tape 61 may be applied to the sheet 16 before each application of the apparatus 10 to assure that slippage does not occur.

In each of the above-described embodiments, the gasket 46 attached to the rim 14 may be configured to distribute any shear forces generated between the skin and rim as the tensile force is applied. This shear force distribution may be accomplished with the use of a silicone gel or inflated membrane or bladder which has a thickness sufficient to allow its surface 70 adjacent the soft tissue to shift laterally with respect to the rim. In this way, the shearing force is distributed along the surface 70 adjacent the soft tissue so that the force is not concentrated at the edge 72 of the rim adjacent the dome. In addition to distributing the shear forces over a larger area, the gel or other flexible rim material provides a cushion to improve the user's comfort and inhibit contusions should an unintentional impact be applied to the dome.

Figure 8:
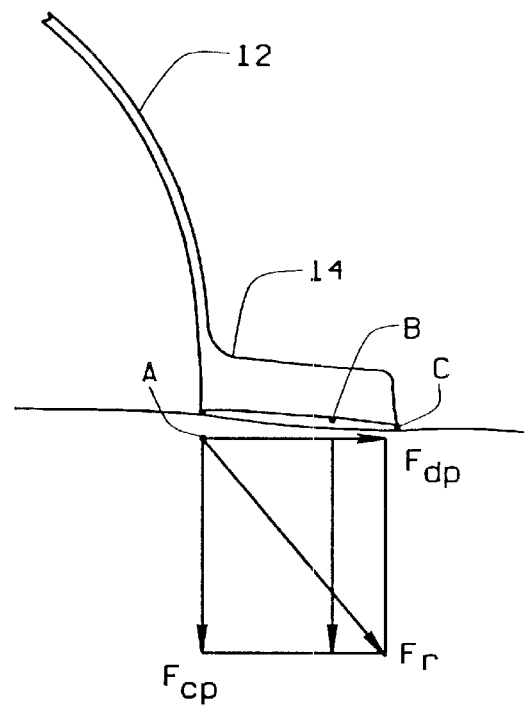
FIG. 8 is a partial cross-sectional view of the dome and rim explaining the shear forces created at the rim.

More particularly, as shown in FIG. 8, and as is explained in greater detail in the *Biomedical Engineering* article referenced above, there are dynamic forces which act on the skin surface under the rim 14 of dome 12. They are illustrated in FIG. 8 as $F_{cp}$ as the counterforce generated by the static effect of the pressure as the vacuum is generated inside the dome 12 which forces it inward towards the skin surface. $F_{dp}$ is the counterforce generated by the dynamic inward pull on the skin surface as it is stretched inwardly by the vacuum effect. This is the shearing force which places the skin surface in tension. $F_r$ is the resultant force, or vector sum of these two forces, exerted on the skin surface by the vacuum within dome 12 and rim 14. At the inner lip of the dome (.A), the resultant force $F_r$ is much greater than the static effect of the vacuum alone. This added effect of the dynamic shear forces and the static pressure force tends to damage the skin just under the inner lip. This was observed by the inventor during limited human trials. For the vacuum dome to be successfully used in cosmetic applications, or indeed for that matter in order to avoid any injury to the patient caused by the vacuum dome, it is desired that this resultant force be accommodated without injury to the patient.

Figure 9:
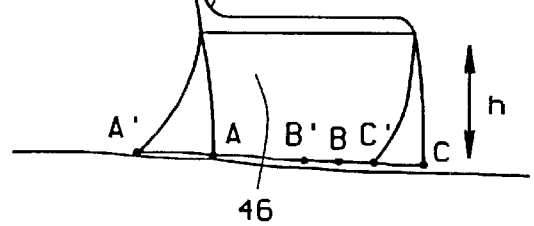
FIG. 9 is a partial cross-sectional view of the dome and rim illustrating the inward displacement of the rim cushion in response to a vacuum within the dome.

As shown in FIG. 9, the dome 12 is supported at a modified rim 14 with an underlying gasket (hereinafter referred to as "cushion") 46 which is sufficiently flexible to allow inward displacement as the skin surface is drawn into the dome 12 by the effect of the vacuum therewithin. As the skin surface is relatively free to "shift" with respect to the rim 14 by the deflexion of cushion 46, the shear force is distributed along the entirety of the lower surface of the rim cushion 46 and is not concentrated at a single point A as is illustrated in FIG. 8 with a rigid rim 14. In other words, points A, B, and C on the rim cushion 46 prior to pulling a vacuum within dome 12 are shifted to points A', B', and C' as the vacuum is generated and the rim cushion 46 deflects. By distributing this shear force across the lower surface of the rim cushion 46, and indeed even beyond as additional peripheral skin is recruited, potential skin damage attributable to this shearing action is minimized.

Desirable attributes for the rim cushion 46 in order to achieve this concentric shifting along the circumferential rim, in the embodiment depicted in FIGS. 8 and 9, includes a height dimension which should accommodate a sufficient amount of deflection desirable to dissipate the shear force. The inventor has found that a height of approximately 2 cm or more in a pressure dome sized to accommodate a typical female breast is adequate. The cushion 46 should have inherent lateral flexibility to allow for repeated bending, deflecting, and rotation. Also, the cushion 46 should be relatively soft, especially along its lower surface, with reduced potential for the formation of any firm or hard skin surface contact area.

Figure 17A:
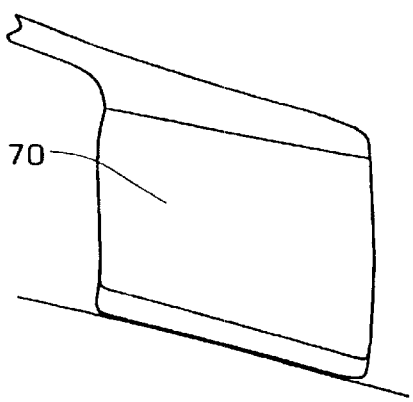
FIGS. 17A, 17B, 17C, and 17D depict various alternatives for mechanical rim cushions.
Figure 17B:
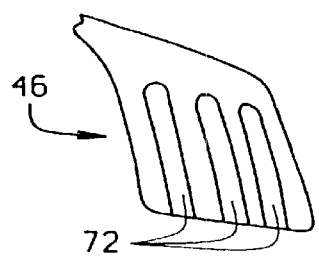
Figure 17C:
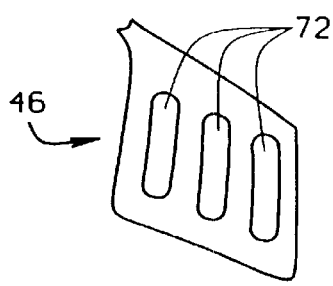
Figure 17D:
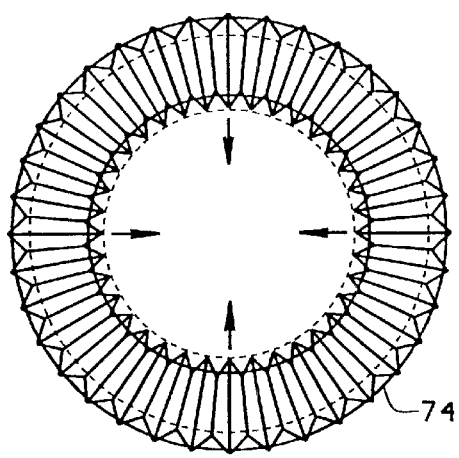

As explained, the embodiment shown in FIG. 9 may be comprised of a gel, inflatable bladder, etc. However, the inventor's concept includes any kind of a mechanical arrangement which would permit relatively uniform concentric displacement. Alternative examples are shown in FIGS. 17A–D and include a foam 70 formed from a polyurethane or other similar substance, a ribbed or "swiss cheese" like construction where various orifices 72 are formed within a semi-rigid or flexible rim cushion 46. Also as shown in FIG. 17D, a bellows 74 or accordion-like construction may be provided which could freely move and accommodate a reduced diameter upon deflexion thereof in response to the pulling of a vacuum within the dome. Other mechanical arrangements which would achieve this desired flexure or displacement would be apparent to those of ordinary skill in the art and are included within the scope of the inventor's concept.

Figure 10:
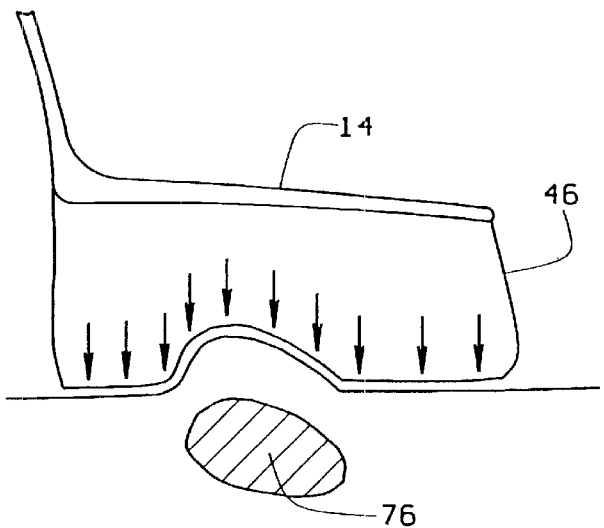
FIG. 10 is a partial cross-sectional view of the rim and rim cushion partially deflected to accommodate a bony prominence.

As shown in FIG. 10, still another physical attribute desirably accommodated by the vacuum dome and rim includes potential points of pressure concentration caused by a rib or other bony prominence 76 underlying the skin surface. As depicted therein, the rim cushion 46 underlying rim 14 should be sufficiently flexible to avoid creating a point of pressure concentration which could contribute to causing pressure sores or the like. This flexibility may be achieved for the use of a fluid-like cushion, an air-filled fluid bladder, a gel-like fluid, or such other construction and materials as would be effective to distribute the pressure substantially uniformly across the skin surface underlying the rim cushion 46.

Figure 11A:
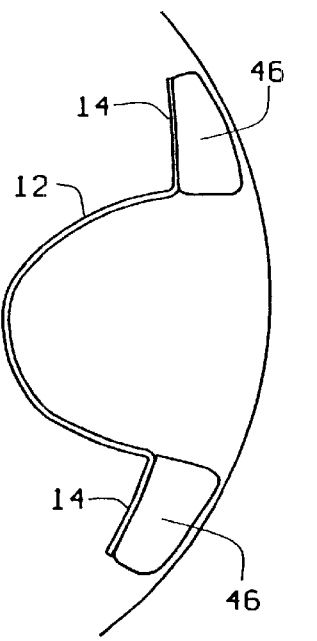
FIGS. 11A and 11B are cross-sectional views of the dome and rim with the rim cushions deflected to accommodate changes in the contour of the body surface.
Figure 11B:
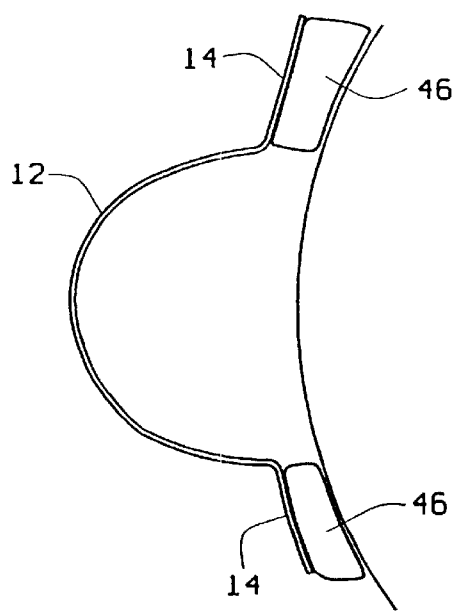

As shown in FIGS. 11A–B, the fluid-like cushion 46 described above, in some applications, should also accommodate an ever-changing contour of the skin surface as the user experiences his activities of daily living. This helps to avoid any potential vacuum loss from within dome 12 which would require reestablishing the vacuum. This helps to ensure reliable application of the vacuum to the intended skin surface without undo involvement with a pump. This ensures reliable results and inconvenience to the patient.

Figure 12:
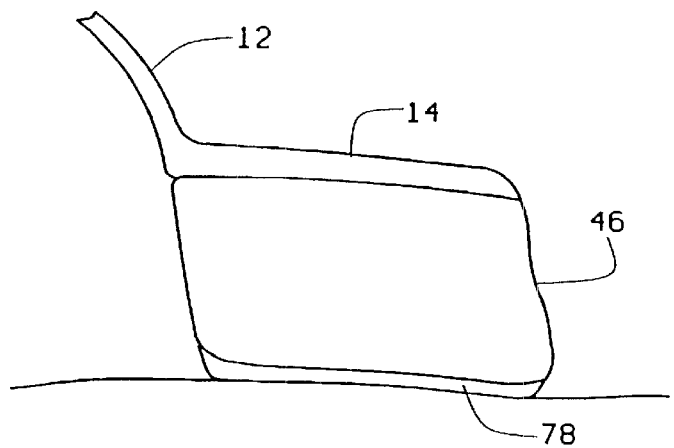
FIG. 12 is a partial cross-sectional view of the dome and rim with rim cushion, with a layer of sticky sole interfaced between the rim cushion and skin.

As shown in FIG. 12, the inventor has also found it desirable to seal the rim cushion 46 to the skin surface through the use of a "sticky" sole interfaced between the rim cushion 46 and the skin surface. This "sticky" sole may be comprised of a number of alternative constructions. For example, the cushion 46 may itself be made of materials which exhibit a sufficiently "sticky" surface property so as to in and of itself provide this "sticky" function. Numerous polymers such as silicone, hydrogels, and many other low durometer synthetic rubbers and gels have this inherent surface property. Alternatively, another substance may be applied to the cushion 46, the underlying skin surface, or any combination thereof in order to achieve this "sticky" seal to ensure that the vacuum within dome 12 is reliably maintained as best as is feasible under the circumstances. This "sticky" sole 78 could also be a sheet or layer of an adhesive material, an adhesive layer may be applied to either the skin surface or rim cushion 46, a tape could be applied between the rim cushion 46 and skin surface, or some other such adhesive effect be achieved in any way which would be well known to those of ordinary skill in the art.

As shown in FIGS. 13A–B, still another application for the vacuum dome 12 with rim cushion 46 is to completely and entirely close an amputation stump. As shown in FIG. 13A, this amputation stump may be a fresh wound and thereby promote healing of the surfaces as well as the growing of soft tissue to overlie any bone which may even be exposed. These kinds of injuries are often encountered where there has been an acute fingertip amputation. Furthermore, the vacuum dome 12 with cushion 46 may also be applied to a previously, but inadequately, healed amputation stump so as to grow additional soft tissue over the bony prominence at the end of the stump. This helps avoid further re-injury, infection, etc.

As shown in FIG. 14, still another application of the vacuum dome 12 with rim cushion 46 is as an aid in endoscopic surgery as is routinely performed in various kinds of plastic and vascular surgery. In this particular application, the vacuum within the dome 12 helps to gently lift a skin flap 80 away from the underlying musculature 82 as an endoscopic dissector 84 is used by the surgeon to carefully separate the skin flap 80. The endoscopic dissector 84 is inserted through a pressure seal 86 within dome 12, through a surgical opening 88 within skin flap 80 in order for the surgeon to reach the area of operation. An endoscopic light source and video camera 90, as known in the art, is also inserted through the dome wall 12 and sealed at 92, and through skin flap 80 at a surgical hole 94. Through either of the openings 88, 94, atmospheric pressure may be introduced under skin flap 80 to cause a pressure differential from within the area 96 and across skin flap 80 into the area 98. This differential pressure serves to assist in the separation of the skin flap 80, as desired. Other surgical tools may also be introduced such as an endoscopic needle holder 100 to facilitate suturing as is well known in the surgical arts. Not only does this assist in separating the skin flap 80 from the underlying tissue, but it also allows for surgical procedures on the deeper structures underlying the skin flap 80 without the necessity for a large skin incision. As is known in the surgical arts, reducing the size and number of incisions and holes reduces scarring and improves the cosmetic result achieved for the patient.

Figure 15:
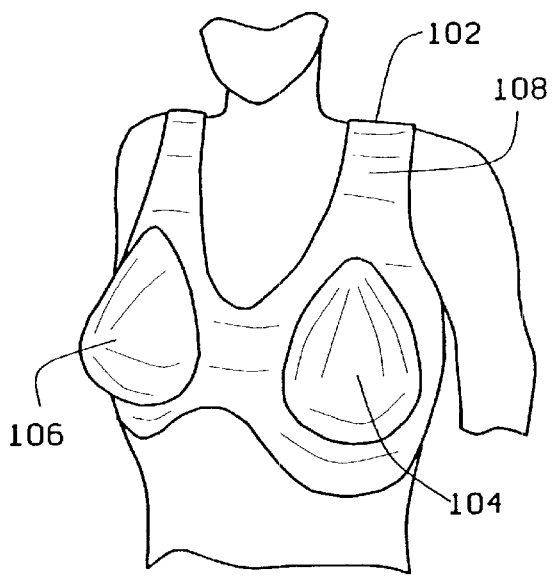
FIG. 15 is a prospective view of a breast enlargement bra utilizing vacuum domes with a surrounding adhesive-coated bra.
Figure 16:
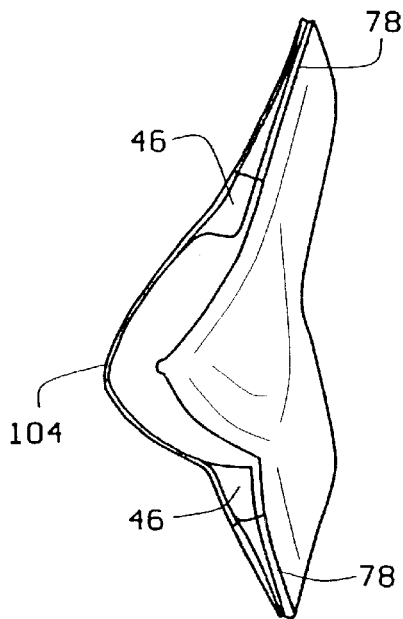
FIG. 16 is a partial cross-sectional view of the bra depicted in FIG. 15 and detailing the vacuum dome, cushioned rim, and surrounding adhesive-coated strap arrangement.

As shown in FIGS. 15 and 16, the "sticky" sole 78 need not necessarily underlie a rim cushion. As shown in FIG. 15, one of the intended embodiments of the inventor's vacuum dome includes a bra 102 including a pair of vacuum domes 104, 106 for increasing a woman's breast size. The sticky sole which provides the seal for the vacuum within vacuum domes 104, 106 may be applied between the straps 108 which surround the domes 104, 106 and, in effect, separated from the rim cushions 46. With this construction, the vacuum dome 104 and rim cushion 46 are mechanically separated from each other, although they should be joined to ensure the seal between the vacuum dome 104 and the underlying skin surface.

There are various changes and modifications which may be made to the invention as would be apparent to those skilled in the art. However, these changes or modifications are included in the teaching of the disclosure and it is intended that the invention be limited only by the scope of the claims appended hereto.

What is claimed is:

1. A dome for applying a vacuum force to a patient's skin surface, said dome having a rim, a rim cushion adapted to support said rim from said patient's skin surface, and a sticky solo adapted to seal the vacuum within the dome against the patient's skin, said sticky sole is adapted to interface between said rim cushion and the patient's skin, and the sticky sole comprises a layer of sticky material.

2. The dome of claim 1 wherein said rim cushion comprises a fluid material adapted to deflect radially.

3. The dome of claim 1 wherein said rim comprises a mechanically collapsible structure adapted to deflect radially.

4. The dome of claim 3 wherein said mechanical structure comprises a flexible material having a plurality of voids therein.

5. The dome of claim 3 wherein said mechanical structure comprises a bellows.

6. The dome of claim 1 wherein said sticky sole substantially surrounds at least the outer portion of said rim cushion.

7. A dome for applying a vaccum force to a patient's skin surface, said dome having a rim, a rim cushion adapted to support said rim from said patient's skin surface, and a sticky sole adapted to seal the vacuum within the dome against the patient's skin, said sticky sole is adapted to interface between said rim cushion and the patient's skin, and said sticky sole comprises a layer of an adhesive substance.

8. A dome for applying a distracting force to a patient's skin surface, said dome being generally semi-spherical in shape and having a circumferential rim, said rim having a radial width for disturbing forces thereacross, and a rim cushion underlining said rim adapted to support said rim and dome from said patient's skin surface, said rim cushion having sufficient flexibility to permit its generally concentric deflection upon application of a reduced pressure within said dome to thereby distribute any shearing force between the rim cushion and the patient's skin, a sticky sole adapted to interface between said rim cushion and the patient's skin, and the sticky sole comprises a layer of an adhesive substance.

9. The dome of claim 1 wherein said rim cushion comprises a fluid material adapted to deflect radially.

10. The dome of claim 1 wherein said rim cushion comprises a fluid-filled bladder.

11. A dome for applying a vacuum to a patient's skin, said dome having a rim, and a sticky sole adapted to interface between said rim and the patient's rim for sealing the space within the dome against the patient's skin, said sticky sole comprises a layer of an adhesive substance.

12. The device of claim 11, further comprising a rim cushion secured to the rim, the sticky sole being applied to a lower surface of said rim cushion and being adapted to contact the patient's skin as the dome is applied to the patient.

13. The dome of claim 12 wherein said rim cushion comprises a fluid material adapted to deflect radially.

14. The dome of claim 12 wherein said rim comprises a mechanically collapsible structure adapted to deflect radially.

* * * * *